United States Patent
Pryce Lewis et al.

(10) Patent No.: US 8,758,658 B2
(45) Date of Patent: Jun. 24, 2014

(54) SYSTEM AND METHOD FOR UNIAXIAL COMPRESSION OF AN ARTICLE, SUCH AS A THREE DIMENSIONALLY PRINTED DOSAGE FORM

(75) Inventors: Wendy E. Pryce Lewis, Lexington, MA (US); Michael J Cima, Winchester, PA (US); Charles W Rowe, Medford, MA (US); Peter A. Materna, Plainsboro, NJ (US)

(73) Assignee: Massachusetts Institute of Technology, Cambridge, MA (US)

( * ) Notice: Subject to any disclaimer, the term of this patent is extended or adjusted under 35 U.S.C. 154(b) by 621 days.

(21) Appl. No.: 12/979,484

(22) Filed: Dec. 28, 2010

(65) Prior Publication Data

US 2011/0187015 A1 Aug. 4, 2011

Related U.S. Application Data

(62) Division of application No. 10/284,430, filed on Oct. 29, 2002, now Pat. No. 7,931,914.

(60) Provisional application No. 60/339,920, filed on Oct. 29, 2001.

(51) Int. Cl.
*B27N 3/00* (2006.01)
*B29C 67/00* (2006.01)
*A61K 9/20* (2006.01)
*A61J 3/10* (2006.01)
*B29L 31/00* (2006.01)

(52) U.S. Cl.
CPC ........... *A61K 9/2095* (2013.01); *B29C 67/0081* (2013.01); *B29L 2031/753* (2013.01); *B29C 67/0051* (2013.01); *A61J 3/10* (2013.01)
USPC ........................................................ 264/109

(58) Field of Classification Search
CPC ..... A61J 3/10; A61K 9/2095; B29C 67/0051; B29C 67/0081
See application file for complete search history.

(56) References Cited

U.S. PATENT DOCUMENTS

| | | | |
|---|---|---|---|
| 4,865,789 A | 9/1989 | Castro | |
| 5,490,962 A | 2/1996 | Cima | |
| 5,587,203 A | 12/1996 | Soda | |
| 5,900,558 A | 5/1999 | Nakamura | |
| 6,280,771 B1 | 8/2001 | Monkhouse | |
| 6,471,992 B1 | 10/2002 | Yoo | |
| 7,276,252 B2 | 10/2007 | Payumo | |

*Primary Examiner* — Michael G Hartley
*Assistant Examiner* — Sun Y Kim
(74) *Attorney, Agent, or Firm* — Rick Matos; Innovar, L.L.C.

(57) ABSTRACT

A uniaxially compressed dosage form manufactured by three-dimensional printing that preserves the predetermined internal architecture of the dosage form while producing an improved surface finish. The compression compacts the dosage form, eliminating at least some of the void space that remains at the end of conventional three-dimensional printing. Surface finish obtained as a result of the uniaxial compression process can be essentially equal to that obtained from conventional tablet pressing. Additionally, the internal structure or spatial variation of composition of the dosage form is preserved during the pressing operation, with geometric shrinkage occurring mostly in the direction of the axis of pressing. Further, as a result of compression, a greater quantity of API can be packed into a given final volume of dosage form.

16 Claims, 11 Drawing Sheets

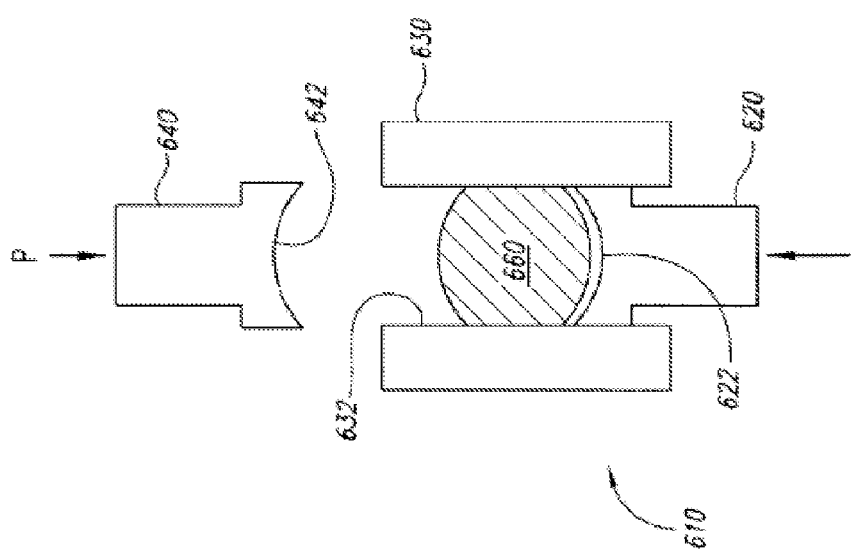
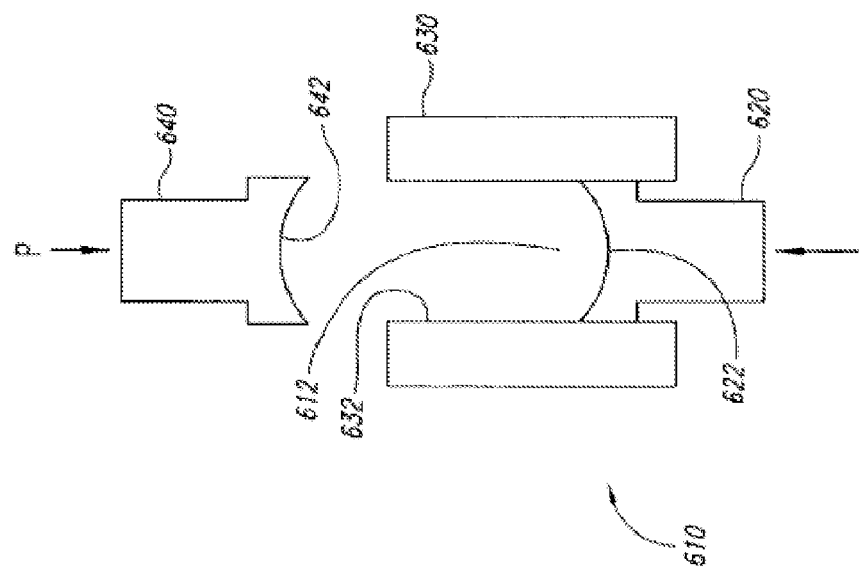

SYSTEM AND METHOD FOR UNIAXIAL COMPRESSION OF AN ARTICLE, SUCH AS A THREE DIMENSIONALLY PRINTED DOSAGE FORM

CROSS-REFERENCE TO EARLIER FILED APPLICATIONS

The present application claims the priority of and is a divisional application of U.S. application Ser. No. 10/284,430, filed Oct. 29, 2002, PCT Application No. PCT/US02/34836, filed Oct. 29, 2002, and U.S. Provisional Application No. 60/339,930, filed Oct. 29, 2001, the entire disclosures of which are hereby incorporated by reference.

FIELD OF THE INVENTION

This invention relates to uniaxial compression of an article, and more particularly, to uniaxial compression of a three-dimensionally printed object such as an oral dosage form.

DESCRIPTION OF THE RELATED ART

One of the most common methods of manufacturing an oral dosage form is by compressing powder into a desired shape using a die and press. This method is inexpensive and suitable for many pharmaceuticals. The powder that is pressed typically includes one or more Active Pharmaceutical Ingredients (API), pharmaceutical excipients (edible inert substances), and substances that help hold the tablet together after completion of pressing. The dosage forms produced by this method have typically been of homogeneous composition or, if they have had any inhomogeneity it has consisted of having a coating on the powder particles before they are pressed, or a coating around the entire tablet after it has been pressed. There has been no detailed or deterministic design of the interior of such a tablet and such design would not be possible with the prior art pressed tablet-manufacturing process.

A newer technique sometimes applied to the manufacture of pharmaceutical dosage forms, which allows the creation of detailed predetermined variation of composition within a dosage form, is three-dimensional printing (3DP). The basic technique is described in U.S. Pat. No. 5,204,055. In three-dimensional printing, which is illustrated in the three-dimensional printing apparatus 100 shown in FIG. 1, a layer of powder is created and then drops of a liquid called a binder liquid are dispensed onto the powder by a technique resembling ink-jet printing. At the places wetted by binder liquid, powder particles are joined to each other and to other solid regions. Then, another layer of powder is deposited and the process is repeated for successive layers until the desired three-dimensional object is created. Unbound powder supports printed regions until the article is sufficiently dry and then the unbound powder is removed. In making a dosage form by three-dimensional printing, an Active Pharmaceutical Ingredient is included in the printed article, most commonly by being contained in a binder liquid which is dispensed onto the pharmaceutical excipient powder. Three-dimensional printing allows for controlled placement of substances within the dosage form, and this has been used to achieve time-dependent release of one or more API, release of API only in an environment of a specified pH, etc. Three-dimensionally printed dosage forms requiring complex release profiles and/or multiple API, as has been described in commonly assigned U.S. Pat. No. 6,280,771.

However, several drawbacks have become apparent with oral dosage forms made by 3DP. One limitation has been that the surface of a 3DP printed part has typically been unacceptably rough as compared to traditionally manufactured pressed tablets. The dimensional scale of the surface texture corresponds to the thickness of the powder layers used in its fabrication. A typical minimum powder layer thickness, for the case of dry powder spread by rollers, is 0.004 to 0.008 inch (100 to 200 microns). This has conflicted with the expectations of consumers accustomed to smooth-surfaced oral dosage forms made by tablet pressing. Oral dosage forms with rough surfaces have been more difficult to swallow than smooth ones, and also rough surfaces have been friable, i.e., have presented possibilities for particles to break off during handling.

Another limitation was that when the API was deposited into the dosage form by being contained in the binder liquid, there have been limitations in terms of how much API could be delivered into the dosage form. Usually the API is delivered by being contained in the binder liquid, and the powder is a pharmaceutical excipient containing no API.

In 3DP the powder has typically been spread to an overall packing density of approximately 50% solid and 50% void. This packing density yields a dosage form that can only include at most 50% by volume of API. API may be delivered into the interstices of the dosage form by solution printing, i.e., with the API being dissolved in the binder liquid that is dispensed onto the powder. If the binder liquid exactly fills the void space and if for sake of example the API is soluble in the binder liquid to the extent of 20% on a volume basis, which is a fairly high solubility among substances of practical interest, then by filling the empty space completely with binder liquid and allowing the volatile part of the binder liquid to evaporate, 20% of the empty space could be filled with the API which had been dissolved in the binder liquid.

The result is that the volume distribution after this first printing becomes 50% excipient, 10% API and 40% void. It is possible to re-print the same region. If it is optimistically assumed that all of the remaining void is accessible to deposited liquid, the result would be to fill 20% of the remaining 40% empty volume, with the result that after evaporation the allocation of volume of the dosage form becomes excipient 50%, API 18%, and void 32%. If still another re-printing were performed, another 20% of that remaining empty volume could be filled, bringing the volume distribution to 50% excipient, 24.4% API content, and 25.6% void. Such a calculation is further illustrated in FIG. 3, which shows more generally that in order to achieve a certain dosage, corresponding pairs of API concentration and saturation parameter are needed.

In 3DP, the saturation parameter describes how much of the void volume is filled with liquid during a printing pass and is typically approximately equal to or less than 100%. Because of the need to deposit significant amounts of API, FIG. 2 extends the definition of saturation to define apparent saturation as extending to values greater than 100%, by using that parameter to refer to multi-pass printing on a given powder layer.

FIG. 3 is based on an assumed dosage form having dimensions of 5 mm diameter by 5 mm high. If one wants to deposit 100 mg of API into a 3DP printed article of these dimensions using an API solution with 20-wt % API concentration, then according to FIG. 2 it is necessary to print to an apparent saturation of 250%. This means that each area or layer would need to be printed, in effect, approximately 2.5 times using a saturation of 100% or in practice 3 times with a saturation of 83%, with intervening evaporation of the volatile part of the binder liquid. FIG. 3 presents the same calculated results as FIG. 2 but with the results presented in a normalized fashion, as mass of API deposited per unit volume of the API-containing region.

One method to eliminate void space in a 3DP printed API-containing article has been with cold isostatic pressing. (Formulation of Oral Dosage Forms by Three-Dimensional Printing, M.S. thesis at Massachusetts Institute of Technology, by Robert Palazzolo, February, 1998) This involved using hydrostatic pressure to press from all directions simultaneously on an article that had been enclosed in a temporary elastomeric bag or mold. It was understood that three-dimensional compression of the three-dimension ODF was required in order to maintain the three-dimensional internal structure and to preserve the release profile of the three-dimensional dosage form. Although cold isostatic pressure reduced some of the void space it did not satisfactorily address these other concerns. Additionally, cold isostatic pressing involved a number of inconvenient process steps, including creation of the temporary elastomeric mold or bag surrounding the printed article, immersion of the mold or bag in a confined liquid to apply the pressure, and removal of the mold or bag. Accordingly, cold isostatic pressing has not been well suited to mass production. Also, while it has improved the surface finish compared to the surface finish of the part after completion of 3DP, resulting in a surface finish as shown in FIG. 4, it has not eliminated surface roughness to an acceptable level.

Accordingly, there is still need for a technique that substantially eliminates void space or reduces void space to the extent desired; allows larger API loading; fits in well with mass production; maintains internal architecture and designed release profiles; and provides a commercially acceptable surface finish for three-dimensionally printed oral dosage forms.

BRIEF DESCRIPTION OF THE SEVERAL VIEWS OF THE DRAWINGS

The invention is described in the following illustrations.

FIGS. 6A-6C illustrate a press suitable for performing the uniaxial compression of the present invention, a tablet-shaped 3D printed article before compression and the resulting dosage form after compression in accordance with principles of the present invention.

DETAILED DESCRIPTION OF THE INVENTION

In the present invention, a three-dimensionally printed article with predetermined internal architecture is uniaxially compressed to provide improved surface characteristics and increased Active Pharmaceutical Ingredient (API) loading while maintaining the designed internal architecture. Aspects of the present invention provide an improved 3DP oral dosage form, including a fully dense oral dosage form with designed internal architecture to provide predetermined release profiles and further including increased API loading as compared to existing 3DP oral dosage forms.

Three-Dimensionally Printed Oral Dosage Form

Figure 1:
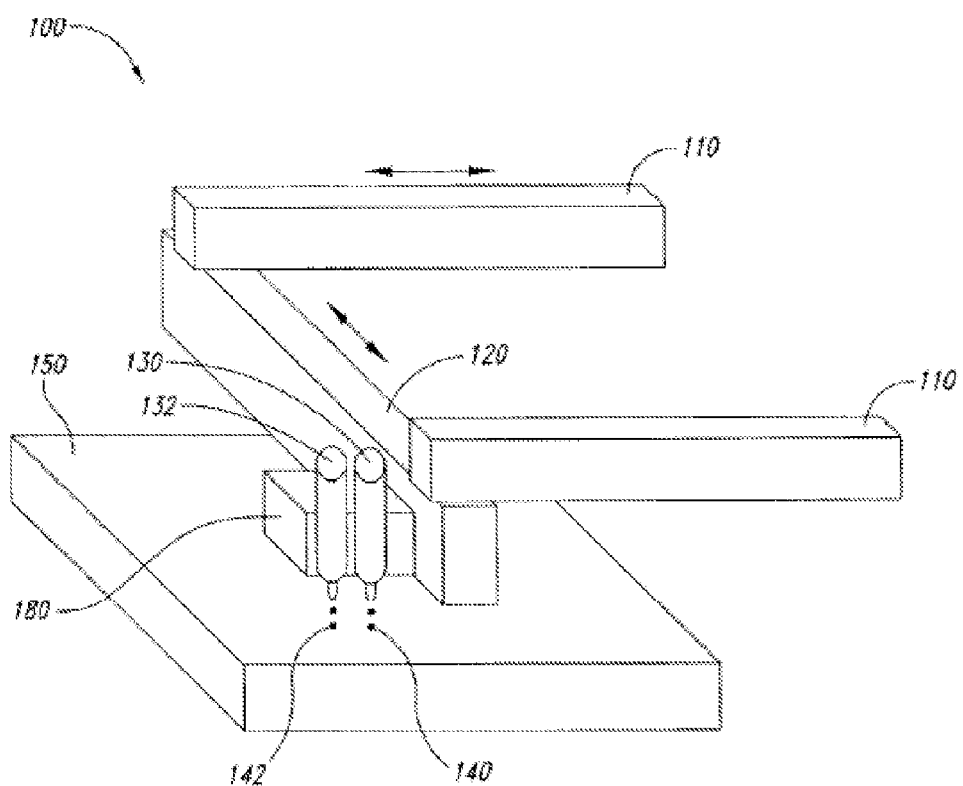
FIG. 1 shows schematically the three-dimensional printing process in accordance with the prior art.
Figure 2:
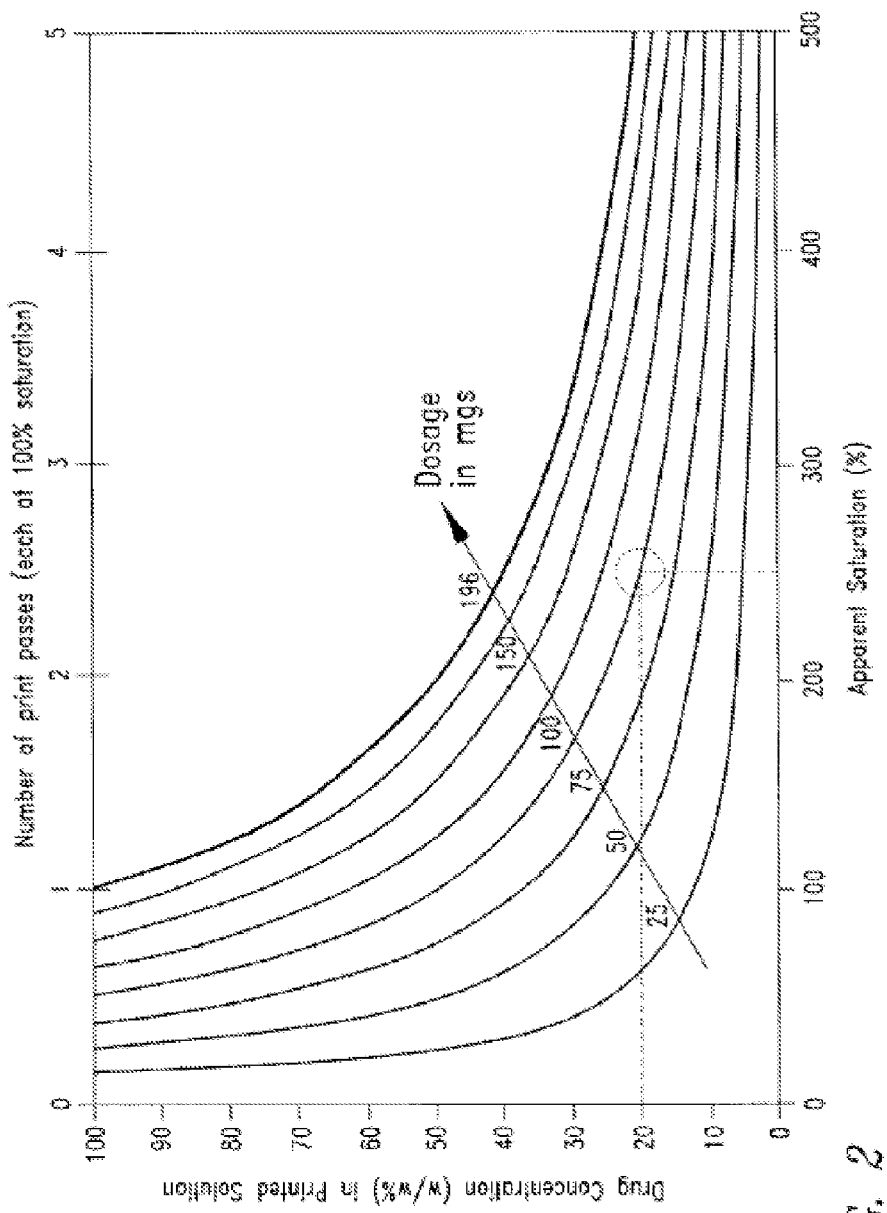
FIG. 2 is a graph illustrating achievable loadings of API in a non-compressed 3DP printed dosage form of specified dimensions, as a function of various printing parameters in accordance with the prior art.

A three-dimensional printer is illustrated in FIG. 1. Layers of powder are spread and in predetermined places a liquid called a binder liquid is dispensed onto the powder by a printhead. For purposes of making dosage forms such as oral dosage forms, the powder is typically a pharmaceutical excipient, i.e., an inert substance that is edible. FIG. 1 further illustrates a printhead 180 mounted movably on a fast axis 120 that is in turn mounted movably on a slow axis 110. Printhead 180 is shown as comprising two dispensers 130 and 132 each of which is capable of dispensing its own binder liquid 140 and 142.

Included in the article in predetermined places is an Active Pharmaceutical Ingredient (API), which may be dispensed by being contained in at least one dispensed binder liquid such as by being dissolved in the binder liquid. Any appropriate type of dispenser including microvalve, piezoelectric drop-on-demand, Continuous Jet with Deflection, or others as are known in the art may dispense the binder liquid.

The use of two or more different dispensed binder liquids for certain dosage form designs described herein allows multiple different compositions or regions within the article and the eventual dosage form. Each binder liquid may contain either or both of a binder substance and one or more API. Different binder liquids can differ from each other in the presence or absence or concentration of one or more API, in the composition or concentration of binder substance, in the content of other inert substances, in color, etc. A binder substance is a substance that causes powder particles to bind to each other.

One way in which binding may occur is that, when the volatile part of the binder liquid evaporates, the binder substance solidifies so as to form a solid that touches or encloses multiple powder particles. Possible binder substances which may be dissolved in the binder liquid include hydroxypropylmethylcellulose, Eudragit L-100 (an anionic polymer based on methacrylic acid and methyl methacrylate), Eudragit E-100 (a cationic acrylic resin based on dimethylaminoethyl methacrylate and a neutral methacrylic acid esters), Eudragit RSPO (a film former based on neutral methacrylic acid esters with a small proportion of trimethylammonioethyl methacrylate chloride, with a 1:40 ratio of quaternary ammonium groups to neutral ester groups), and Eudragit RLPO (same, with a 1:20 ratio) (all available from Rohm-Pharma).

Possible solvents that can be used as the volatile part of the binder liquid include water, ethanol, methanol, isopropanol, other alcohols, chloroform, and acetone. Possible excipients include Eudragit RSPO, microcrystalline cellulose, hydroxypropylmethylcellulose, mannitol, xylitol, sorbitol, dicalcium phosphate, lactose, glucose, dextrose, fructose and other sugars. Further examples are listed in Handbook of Pharmaceutical Excipients, Third Edition, by Arthur H. Kibbe (2000). A suitable range of powder particle size may be determined by sieving.

A possible external geometry of a dosage form may be cylindrical with rounded convex surfaces at each end of the cylindrical region. The 3D printed article may achieve this shape by programming of appropriate patterns for printing on individual layers. One build pattern for this operation is shown in FIG. 5 showing such an article made from a plurality of layers, in this embodiment, 9 layers for one curved cap 510, 25 layers for the cylindrical region 520, and 9 layers for the other curved cap 530.

Figure 5:
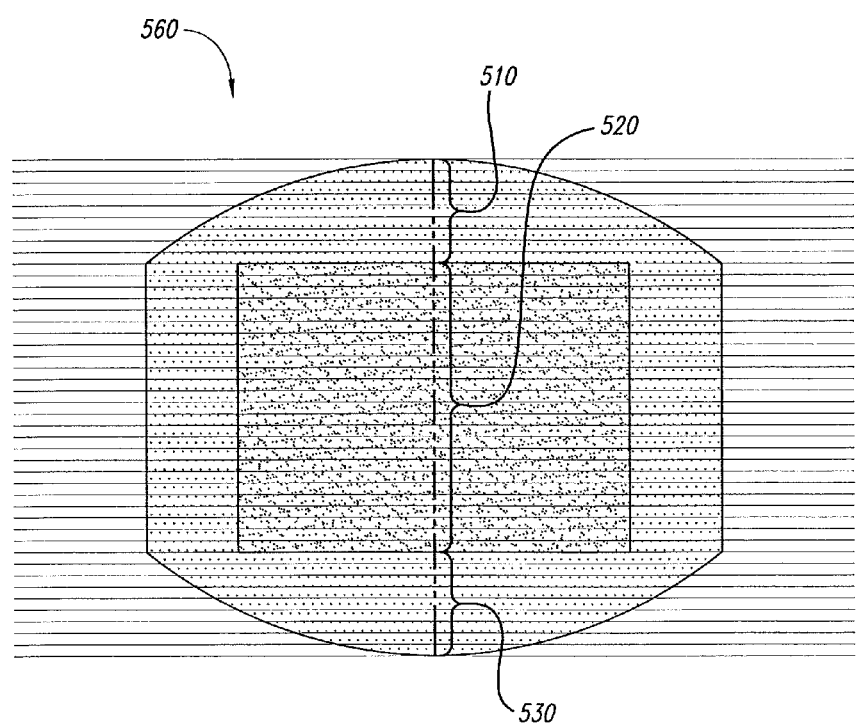
FIG. 5 illustrates the layered structure used during 3DP printing, for a typical shape of dosage form in accordance with principles of the present invention.

In FIG. 5, the symmetry axis of the cylindrically symmetric dosage form and corresponding article coincides with the vertical build direction in the 3DP process, although this is not necessary. In general, a dosage form and corresponding article such as a 3DP printed article may be cylindrical with either flat or rounded top and bottom surfaces, or rectangular prismatic with either flat or rounded surfaces, elliptical prismatic with either flat or rounded surfaces, ellipsoidal, spherical, or could have any general shape of cross-section and any general shape of end or cap.

After a process such as 3DP produces articles, a harvesting operation (not illustrated) may be performed to separate the articles from the entire printed bed, some of which may still be loose powder. Harvesting may include an operation such as scraping or separating near the bottom of the build bed, such as by a blade. In order to facilitate this, several layers of loose unprinted powder may be provided at the bottom of the build bed so that the articles do not stick to the underlying solid surfaces, as is known in the art. De-dusting may then be performed.

De-dusting is a more detailed and small-scale removal of powder particles that may be loosely adhering to the surfaces of articles that have been harvested at the end of the 3DP process. De-dusting may include such operations as tumbling the articles or exposing them to a jet of gas or particle-bearing gas, as is known in the art. A de-dusting operation may result in better smoothness and quality of the surface finish of the dosage form after the later step of uniaxial pressing.

After harvesting, the articles may be placed individually into cavities in a press suitable to exert significant compressive force on the printed article from one direction such as by means of a ram, while in substantially all other directions the printed article is confined against rigid surfaces. For a shape of dosage form comprising a cylindrical portion and possibly curved end portions, all having cylindrical symmetry, the easiest axis along which to perform uniaxial compression on the article such as a 3DP printed article is the cylindrical axis. Even if the article lacks cylindrical symmetry or even any symmetry, it can still be compressed according to the present invention.

The article may be manufactured with a dimension, along the axis of compression, which is greater than the desired final dimension of the dosage form by a factor that is determined by the expected extent of compression. The dimensions of the article in a cross-section perpendicular to the pressing axis may be just slightly smaller than the interior dimensions of the die assembly, so as to allow for easy insertion of the article into a die cavity. The axis of compression may coincide with the vertical (layer-to-layer) build direction of the 3DP printing process.

Uniaxial Compression of Three-Dimensionally Printed Oral Dosage Form

According to aspects of the present invention, an improved three-dimensionally printed oral dosage form is described herein. The fully dense ODF retains the predetermined internal architecture to a predictable degree, thus release profiles, including multiphasic release profiles, may be obtained. Additionally, the uniaxial compression of the ODF allows increased API concentrations even while retaining the internal architecture of the ODF.

Accordingly, as illustrated in FIG. 6, one embodiment of a uniaxial press includes a die 610 having a receiving cavity 612 whose lower features correspond to the desired shape of the bottom of the compressed dosage form. The die 610 may be made of two close-fitting parts, i.e., a lower die 620 and a sleeve 630. A design in which lower die 620 is separate from the sleeve 630 allows for ejection of the dosage form after pressing by moving the lower die 620 and the sleeve 630 relative to each other. In an alternative embodiment, a single-piece cavity having an integral lower die 620 and sleeve 630 are used to uniaxially compress the dosage form.

The lower die 620 has a lower die surface 622 facing the article 660. A ram 640 having a ram surface 642 facing the article 660 presses on the surface of article 660 that is away from lower die 620. The die or receiving cavity 612 may have a bore of constant cross-section for at least part of its distance. Ram 640 may be adapted to slide in a close-fitting manner into the bore of die 610. The bore and the ram may have cylindrical symmetry with the axis of the cylindrical symmetry being parallel to the axis of motion.

The bottom die 620, sleeve 630 and ram 640 may closely confine the printed article 660 from all directions with no significant holes or leakage. The outside diameter or shape of the ram 640 and the inside diameter or shape of the sleeve 630 may be such as to provide a close sliding fit, and the same may be true for the outside diameter or shape of the lower die 620 and the inside diameter or shape of the sleeve 630 if these are separate parts from each other.

Non-circular cross-sections of the ram and die are possible, including shapes without symmetry. The ram, die and sleeve may fit closely with respect to each other such that the only places facing the printed article which are not perfectly solid are those small gaps where sliding motion takes place between closely-fitting parts.

Surfaces 622 and 642 define the lower and upper surfaces of the eventual compressed dosage form 670 and may be shaped according to the desired final shape of the dosage form. Either or both of these surfaces may be made curved in order to produce curved surfaces of the dosage form. Alternatively, either or both of these surfaces may be flat.

Lower die 620, sleeve 630 and ram 640, or at least their surfaces 622, 632 and 642 which contact the article, may be made so as to be harder than the hardness of the article produced by the 3DP process. All of the surfaces 622, 632 and 642 that contact the printed article during compression may be smooth with a specified surface finish so that the after-compression surfaces of the dosage form are similarly smooth to the degree or smoothness desired.

A non-smooth surface may sometimes be desirable to produce identifying characters or similar markings, known as trade dress, on some surfaces of tablets by means of the pressing operation as is sometimes done in conventional tabletting. To accomplish this, features such as projections or recesses can be incorporated into lower die surface 622 or ram surface 642 or both. The article 660 may be printed from 3DP printing instructions such that its shape and dimensions correspond to the shape and dimensions of the lower die surface 622 and ram surface 642, which will result in relatively little rearrangement of printed material occurring during compression.

After the article 660 such as a 3DP printed article is placed in the cavity 612, the ram 640 may be brought down upon the article 660. A suitable pressure for pressing the article such as a 3DP printed article in order to eliminate essentially all the void space is approximately 15,000 lbf/inch{circumflex over ( )}2, which is defined as compression force P divided by the cross-sectional area of the bore of the cavity 612 or the maximum cross-sectional area of the printed article 660 in any cross-section taken perpendicular to the axis of pressing.

For typical excipient powders, binder substances, and the like, such a pressure may compact most of the void space which remains after 3DP and maintain or cause adhesion of the particles and deposited substances to each other and resulting in a dosage form which is almost fully dense. It is believed that smaller compressing pressures even in the range of approximately 5,000 psi would still be suitable to smooth the surface and remove almost all of the void, at least for some powders. Compression times on the order of seconds are more than adequate to accomplish the desired compaction. Compression such as to remove only some of the void space is also discussed later. This compression operation transforms article 660 such as a 3DP printed article into dosage form 670.

The invention is further illustrated but is in no way limited by the following Examples.

Example 1

Improved External Surface Smoothness of 3DP ODF Using Uniaxial Compression

This Example illustrates the external surface of a three-dimensionally printed dosage form that has been uniaxially compressed after being initially produced by 3D printing. Articles were printed using a three-dimensional printing system as already described. The pharmaceutical excipient powder, binders and internal printing structure and printhead are further described herein.

After the 3DP operation, which left rough surfaces containing steps corresponding to the thicknesses of the powder layers used in the 3DP printing process, some of the 3DP printed articles were uniaxially pressed at a pressure of 15,000 psi. This pressing was performed using a stainless steel tablet die with an internal diameter of 11 mm and custom plungers with concave surfaces to match the intended contour of the tablet caps, having a radius of curvature of 1.32 cm resembling what is shown in FIG. 6.

The shape of the upper and lower surfaces of the article such as a 3DP printed article corresponded closely to the shape of the upper and lower dies. The surface of the die which contacted the article such as a 3DP printed article was polished with 2400 grit abrasive to attain a surface smoothness of approximately 1 microinch rms or smoother. The surfaces 622, 632, 642 pressing on the printed article, being made of stainless steel, were all substantially harder than the printed article or any substance present in the printed article.

The external surface of the dosage form after compression exhibited greatly improved smoothness compared to what had existed after the 3DP process alone. In fact, the surface finish after compression was essentially equivalent to what is obtained from commercially available alternatives such as conventionally pressed tablets made by pressing loose powder in a single step.

Figure 7A:
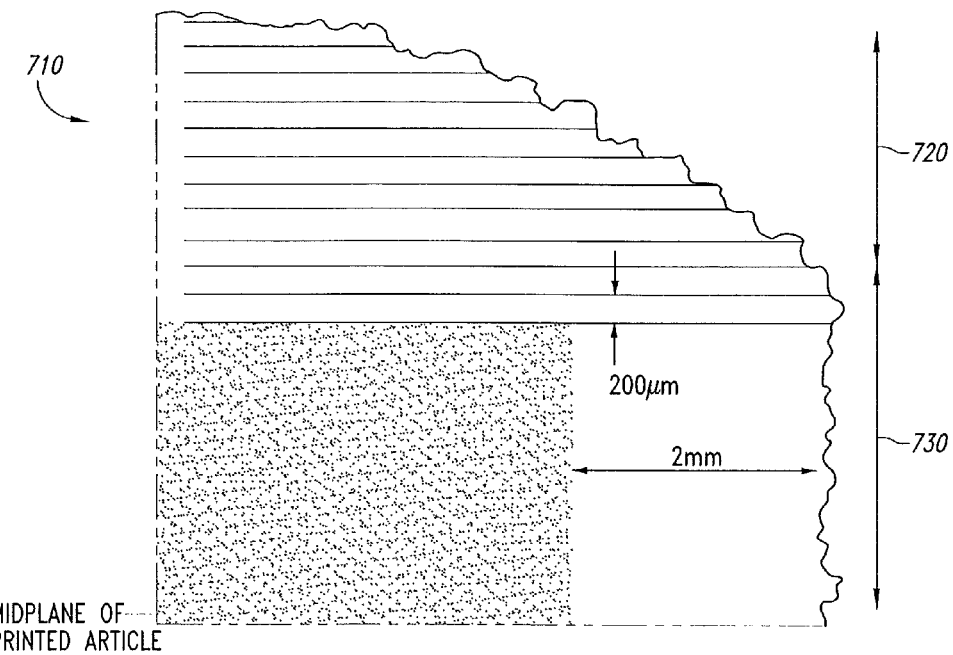
FIGS. 7A and 7B illustrate a cross-section of a 3D printed article before uniaxial compression and a corresponding dosage form after uniaxial compression in accordance with principles of the present invention.
Figure 7B:
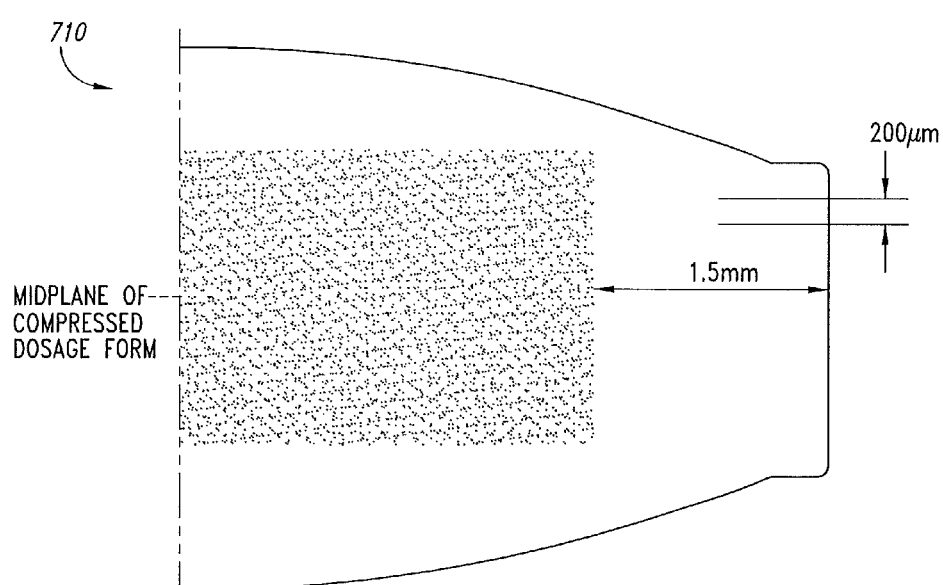

FIG. 7A illustrates a typical cross-section of the surface of tablets prior to pressing, having steps that were of the size scale of the thickness of the layers of powder used during 3DP. FIG. 7B illustrates a cross-section of the external surface of the ODF corresponding to the after-compression surface.

The external dimensions of non-compressed and compressed samples were measured with digital calipers, and these measurements are given in Table 1. Girdle refers to the height, in the axial direction, of the cylindrical portion of the article or dosage form excluding the curved end caps.

TABLE 1

AVERAGE EXTERNAL DIMENSIONS OF ARTICLE AND DOSAGE FORM BEFORE AND AFTER COMPRESSING

|   |   | Overall Height | Outside Diameter | Height of Girdle |
|---|---|---|---|---|
| a | Un-pressed | 8.70 mm +/− 0.1 | 11.22 mm +/− 0.1 | 5.26 mm +/− 0.1 |
| b | Pressed | 4.59 mm +/− 0.01 | 11.16 mm +/− 0.01 | 2.58 mm +/− 0.01 |
|   | % (b/a) | 52.8% +/− 0.8% | — | 49.0% +/− 1.2% |

The volume shrinkage and dimensional shrinkage which occurred during uniaxial compression were approximately 50% in volume and in dimensions such as overall height and the height of the girdle which are measured along the axis of compression. This can be attributed to the collapsing of void volume that was present in the 3D printed article.

The improvement of the surface finish can be attributed to very localized rearrangement of powder particles during pressing. It is believed that the rms (root-means-square) roughness of the surface of the compressed dosage form of the present invention is similar to the rms roughness of the surfaces 622, 632 and 642 that press on the article during the compressing process. FIG. 7B illustrates the surface finish of the dosage form of the present invention after compression.

From actual photographs of compressed ODF's, the surface roughness can be estimated as being smoother than approximately 2 microns rms (root-mean-square), which corresponds to a peak-to-valley dimension of between 2 and 3 microns. These descriptors are believed to be roughly comparable to the surface finish of the die and ram surfaces that pressed on the dosage form. This surface finish of the dosage form of the present invention is significantly better than the surface condition of the printed article before uniaxial compression, which had steps of the powder layer thickness, approximately 200 microns.

Figure 4:
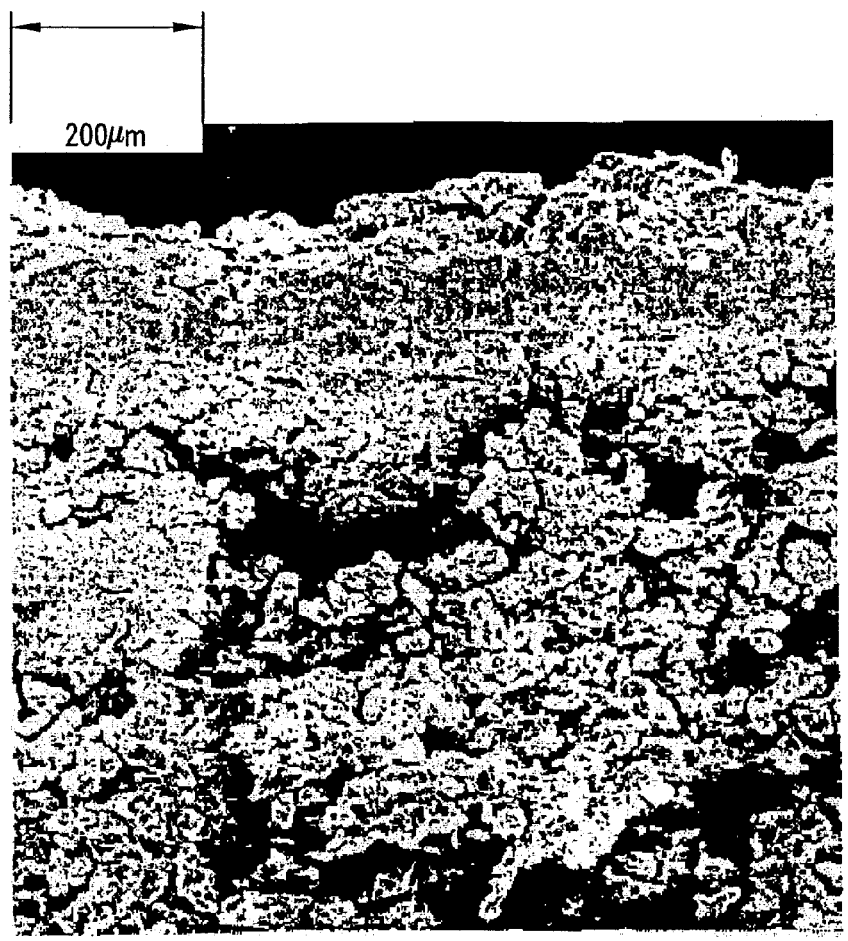
FIG. 4 illustrates an enlarged cross-section of a surface produced by a cold isostatic pressing process in accordance with the prior art.

This surface finish of the dosage form of the present invention is significantly improved over cold isostatic pressing. Additionally, uniaxial compression preserves the internal architecture of the ODF while providing superior surface finish and increased density. In the photograph of a prior art isostatically pressed surface in FIG. 4, the variation in height from a local peak of the surface to the deepest nearby valley can be estimated as being 83 microns. The corresponding rms (root-mean-square) variation can be estimated as 60 microns.

Cold isostatic pressing failed to produce an acceptable surface finish in part because cold isostatic pressing includes a compliant elastomeric bag or mold pressing on the surface of the article, wherein the hardness of the elastomeric bag or mold was less than the hardness of the article and the powder particles contained in it. In contrast, the technique of the present invention uses smooth hard metal pressing surfaces which may be harder than the article such as a 3DP printed article and its powder particles, and therefore should be more suitable to push powder particles into a configuration giving an extremely smooth surface.

Example 2

Integrity of Internal Structure of 3DP ODF Maintained in View of Uniaxial Compression Three-dimensional printing provides the ability to create internal structure and compositional variation in dosage forms. Accordingly, this Example is intended to illustrate how the internal structure of a 3D printed dosage form can be maintained while a dosage form undergoes uniaxial compression. The tablets in this Example were the same as those in Example 1. The outer shape of these dosage forms was circular-cylindrical with curved end caps.

As far as internal composition, these dosage forms comprised an inner API-containing region that, in the illustrated cross-section, had a rectangular cross-section and its full three-dimensional shape was a circular cylinder. This circular-cylindrical API-containing region was completely surrounded by an outer non-API-containing region that occupied the remainder of the dosage form not occupied by the inner region. The articles were constructed in a layered structure having top-to-bottom symmetry around a midplane, as well as cylindrical symmetry around a central axis. FIG. 5 illustrates a cross-section of the exemplary ODF. As previously noted, 9 layers making up the top curved surface 510, 25 middle layers making up the girdle of the shape 520 and 9 layers making up the bottom curved surface 530, for a total of 43 layers or 8.6 mm in as-printed height. The middle 25 layers made up the maximum outside diameter or cylindrical portion having an outside diameter of approximately 11 mm. Into each of these middle 25 layers, rings of the outer wall regions (outside diameter=11 mm, inside diameter=7 mm) were first printed, and circular regions of the API-containing region (outside diameter=7 mm) were then printed.

The powder used in fabricating these samples was 50-wt % microcrystalline cellulose (particle size between 38 and 53 microns) mixed together with 50-wt % lactose (particle size between 53 and 74 microns), having an as-spread packing fraction of 0.428, and using a layer height of 200 microns. Liquids were dispensed by a Continuous-Jet printhead, having an orifice of 50-micron orifice diameter, and droplets were optionally charged and deflected to control whether individual drops were printed onto the powder bed.

The outer region or ring region in the 25-layer-thick middle was printed with a solution of 5-wt % Eudragit L100 in ethanol. The curved end cap regions were also printed with this binder liquid. The Eudragit L100 served as a binder substance, in this case a substance that, upon evaporation of the volatile solvent, binds particles together by solidifying around adjacent particles or by solidifying so as to form necks at and near the contact points of adjacent particles. A saturation parameter of 1.3 was achieved in this outer region, giving a volume fraction L100 of theta (L100)=0.024. Thus the void space or porosity remaining in this section was unity minus the as-spread packing fraction of powder minus the fraction filled by deposited solid substance, or 1−0.428−0.024=0.548, meaning that the outer region was 54.8% porous.

The interior API-containing region was printed with a binder liquid containing API (at a 22% concentration) along with a very small concentration of a marker substance. In this API-containing region the binder liquid did not actually contain a binder substance because it was unnecessary to actually bind the powder together, since the outside of the article was held together by the binder substance used to print the surrounding outer region.

The marker substance enabled easy identification of a boundary between regions of differing composition, such as might be desired for time-release of an API. The marker substance was 0.05-wt % fluorescein sodium salt (Sigma Chemical Co.), which is an easily detectable fluorescent dye that emits green light when illuminated by ultraviolet light. Printing parameters for the API-containing region were 25 layers, 200 microns layer height, line-to-line spacing of 120 microns, API-printed region 7 mm in diameter, saturated to a saturation parameter of 1.0. The volume fraction of API in this region was given by theta (API)=0.107. Thus the void space or porosity remaining in this inner region was 1−0.428−0.107=0.465, meaning that the inner region was 46.5% porous.

After printing, the dosage forms were allowed to dry completely and some of the samples were then uniaxially pressed at a pressure of 15,000 psi using the previously described stainless steel tablet die with diameter of 11 mm, and custom plungers having convex surfaces having a radius of curvature=1.32 cm to match the contour of the tablet caps. All of the samples were then mounted in low-viscosity epoxy and cross-sectioned to observe the internal detail and surface finish. The fluorescein in the sections printed with that substance fluoresces under ultraviolet light and therefore makes it possible to easily distinguish between the two regions of the tablet. The cross-sectioned dosage forms were photographed under ultraviolet light and the dimensions of the boundaries between the fluorescent or non-fluorescent features or overall dimensions were measured by digital analysis of the light intensity, at the fluorescent wavelength, of pixels in photographs of these cross sections.

FIGS. 7A and 7B illustrate the cross sections of the non-compressed articles and the compressed dosage forms. It could be seen in the actual photographs that before pressing a clear boundary between existed between the region printed with one binder and the region printed with the other binder, and after compression a clear boundary still existed but in a slightly different location. Internal features of the noncompressed articles and the compressed dosage forms have been characterized by their dimensions before and after compression, as given in Table 2.

TABLE 2

INTERNAL MEASUREMENTS OF NON-COMPRESSED 3DP PRINTED ARTICLES AND COMPRESSED DOSAGE FORMS

|   |   | Height of Fluorescent Region (mm) | Diameter of Fluorescent Region (mm) | Wall Thickness (mm) |
|---|---|---|---|---|
| a | Un-pressed | 5.00 +/− 0.1 | 7.1 +/− 0.1 | 2.06 +/− 0.1 |
| b | Pressed | 2.47 +/− 0.12 | 8.16 +/− 0.16 | 1.50 +/− 0.08 |
|   | % (b/a) | 49.4% +/− 2.9% | 115% +/− 3.4% | 72.8% +/− 7% |

The major change in dimensions of internal features resulting from compression was a shrinkage of dimensions along the axis of compression, such as the height of the fluorescent region. This normalized result is very similar to the normalized changes of the external girdle and overall external height dimensions as reported in Table 1. In the other principal direction, i.e., radial, it can be seen that the boundary has moved slightly outward in the radial direction, which indicates that there has been rearrangement of the material during the pressing operation.

In both Example 1 and 2, internal structure was preserved despite deductive teachings that it would not. The one embodiment shown in Example 1 and 2, the core region was printed with enough deposited API that it had a somewhat higher solids content (a somewhat lower void fraction) than did the shell region. Resulting in the boundary between the API region and the excipient region moving slightly in the radial direction as a result of compression. In FIG. 7B as compared to FIG. 7A, the boundary is not in the same radial position. Nevertheless, the boundary still is about as distinct afterward as it was before. The motion of material inside the dosage form during this compression process was more than just one-dimensional, i.e., there was at least a little bit of radial motion.

In another embodiment, if the shape of the end cap region is other than flat, there is going to be some multi-dimensionality of local powder particle motion during the uniaxial compression process. This would be true whether or not the 3DP printed shape of the end cap is the same as the shape in the die that will meet it. Therefore, even though within the end cap region there almost certainly was some two-dimensionality of local particle motion during the uniaxial compression process, in the main part of the dosage form (which is closer to an ideal one-dimensional geometry as far as what can be expected to happen during the compression process), there was not any significant disturbance of the region-to-region boundary, i.e., the boundary was well maintained.

As shown in Table 2, material has moved from a region of high density and low void fraction to regions of lower density and higher void fraction. In the region with greater initial porosity, more void space had to be collapsed by compression, which induced material to move into that region from the higher-density region. Before pressing, the central region had a higher density than the outer region, because its void spaces were partly filled by a binder liquid containing a substantial combined concentration of various substances principally API, and the void fraction there was 46.5%. In the outer regions the void spaces were less filled because that region was printed by binder liquid containing only a relatively small concentration of a binder substance, and the void fraction there was 54.8%.

Thus, rearrangement of material in directions other than the axis of uniaxial compression was much smaller than the dimensional changes along the axis of compression, but it did occur. This is explainable based on an understanding of the respective void fractions of individual regions. It is also possible that in the region of the curved end caps, which was a somewhat more complicated and multi-dimensional geometry, there may have been some rearrangement of material because in that geometry compression in one direction would have to be associated with some motion of material in other directions due to the more multi-dimensional geometry. It was observed that, at least in the somewhat one-dimensional cylindrical region, even though in directions other than the principal compression direction there was minor rearrangement of material and movement of the location of the boundary, the boundary itself remained essentially as sharp as it was before compression.

The void fraction can be defined as the fraction of volume that is not occupied by solids. A part such as a 3DP printed article has a density, which its weight divided by its volume. It is also possible to determine what would be its solid density, i.e., its density if it were fully solid and contained no void. For pure substances the solid density is generally known, and for mixtures or combinations of substances the solid density can be calculated from the solid densities of the individual components and their respective composition fractions, as is known in the art.

For example, in a article such as a 3DP printed article which may comprise a powder, some binder substance and some API, each of which has its own solid density, it is necessary to use a weighted average to combine them to calculate the theoretical solid density. Whatever is the difference between the observed density and the theoretical solid density represents void. Void fraction is usually expressed in nondimensional form, i.e., what fraction of the overall volume of the dosage form is empty space. In the dosage forms of this Example, after the described compression, the void fraction was less than 5%.

Although in this Example the outer region did not contain API, in general the outer region could be of any composition that is different from that of the interior region, i.e., it could contain no API or a different concentration of same API or different API.

Example 3

Uniform Initial Void Fraction to Minimize Impact of Uniaxial Compression on Internal Architecture In the preceding example, during the compression there was some motion of the interface or boundary between the two regions in a direction perpendicular to the axis of compression, in this case, radial motion. Such motion can be estimated during the design stage of a dosage form and the dosage form can be designed so as to compensate for such expected motion of the interface or boundary during compression. In the previous example, the radially outward motion of the API/non-API interface occurred because the as-printed API-containing region had relatively less void, and the as-printed outer region had relatively more void, even though both ended up being essentially fully dense after compression. Therefore, more removal of void volume had to occur in the outer region than in the inner region, and so material squeezed and moved out from the more-dense region into the less-dense region. However, it may be desired that there be no such motion of the boundary and no need for dimensional compensation in the design of the dosage form. It is believed that if, in the article such as a 3DP printed article, both regions had had the same initial void fraction, then during compression the interface or boundary would essentially not have changed its position in a direction perpendicular to the axis of compression such as the radial direction.

Therefore, this example is a case in which both regions are printed to be of equal void fraction as-printed. The inner region comprises API printed onto the powder and the outer region comprises an inert printed substance or binder substance printed onto the powder for the purpose of filling void to the same extent as in the API region even though simply for purposes of binding it might not be necessary to have so much solid substance deposited in this region. This equality or matching of void fractions is expected to cause the interface or inter-region boundary after uniaxial compression to remain in essentially the same radial location or location in a plane transverse to the axis of compression as it occupied before printing, because the equality of void fractions means that during compression there should be essentially no need for rearrangement or motion of material in any direction other than along the direction of uniaxial compression, at least for geometries which are not extremely complicated.

In a dosage form viewed after compression, there would be no direct way of knowing where the inter-region interface or boundary was when the article was 3DP printed, or whether during compression the interface or boundary moved in a direction perpendicular to the axis of compression such as the radial direction. After compression, essentially all of the void space would be gone from all regions, and it would not be immediately evident what the void fractions of individual regions had been before compression. However, it is still possible to infer whether the technique of this Example was used and whether those void fractions of individual regions had been equal to each other, namely by measurement of the composition of respective regions of the compressed dosage form.

After compression, each region has a fraction of its content that is original powder and also has a fraction of its content that is other solid substances that were delivered onto the powder by one or more binder liquids. At the earlier stage of the article after the conclusion of 3DP before compressing, each region contained a combination of original powder, delivered solid substances and void. In a spread powder bed, the fraction of powder is essentially constant everywhere because of properties of spreading and settling of powders in general or of the specific powder being used. Therefore, since the three fractions must add up to unity, the void fraction and the fraction of delivered solid substance had to be directly related to each other.

At the later situation when compressing has eliminated all voids, if the fractions of delivered solid substances in various regions are equal to each other, this indicates that before compression the void fractions in the various regions also were equal to each other. This in turn means that the compression of the article to form the dosage form would have taken place with essentially no moving of the interfaces or boundaries between regions, in directions perpendicular to the axis of compression. This would have provided the special convenience of design that comes from knowing that during the compression process the interface would remain essentially unmoved in directions perpendicular to the axis of compression. In the case of an API-containing region, the delivered solid substances may be at least partly API. In the case of regions not containing API, the delivered solid substances may be binder substances or other inert substances. The ability to determine that void-fraction-matching is used in an article by observing component-fraction-matching in the compressed dosage form is true no matter how many regions or compartments are designed into the article.

Example 4

3DP Oral Dosage Forms with Complex Internal Geometry

This example illustrates more complicated geometries that could also be manufactured by 3DP and compressed by uniaxial compression. One such example is a combination of regions each of which is contained inside others in the form of nesting. All the nested regions may, for example, be concentric. This is shown in FIGS. 8A-8C.

Figure 8A:
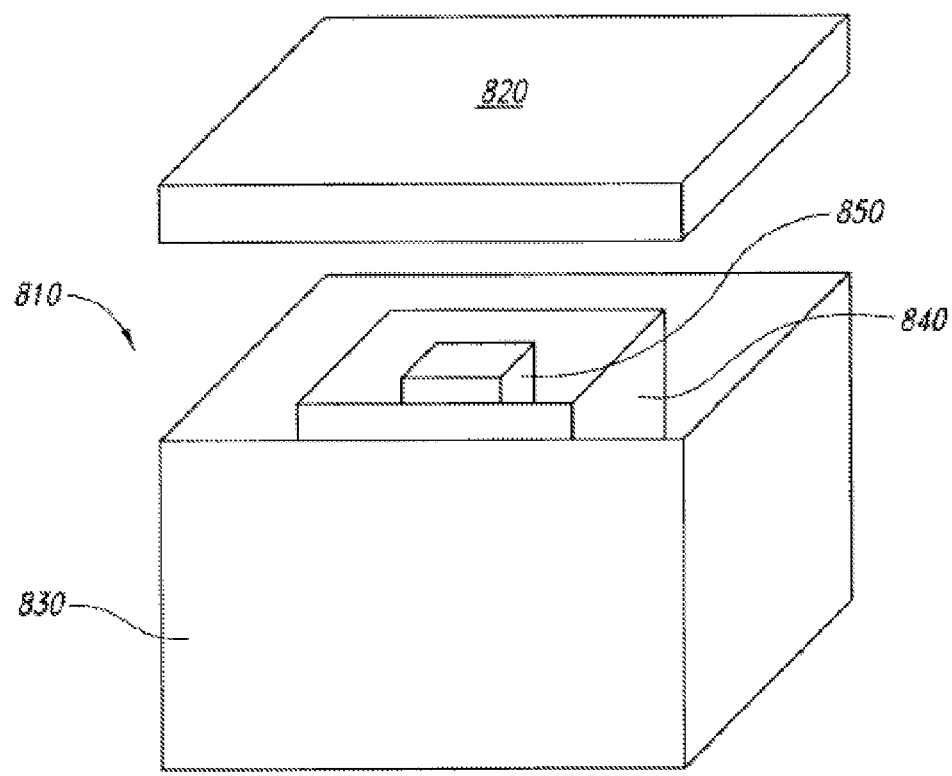
FIGS. 8A-8C illustrate designs of compressed dosage forms comprising more than one interior region in accordance with principles of the present invention.
Figure 8B:
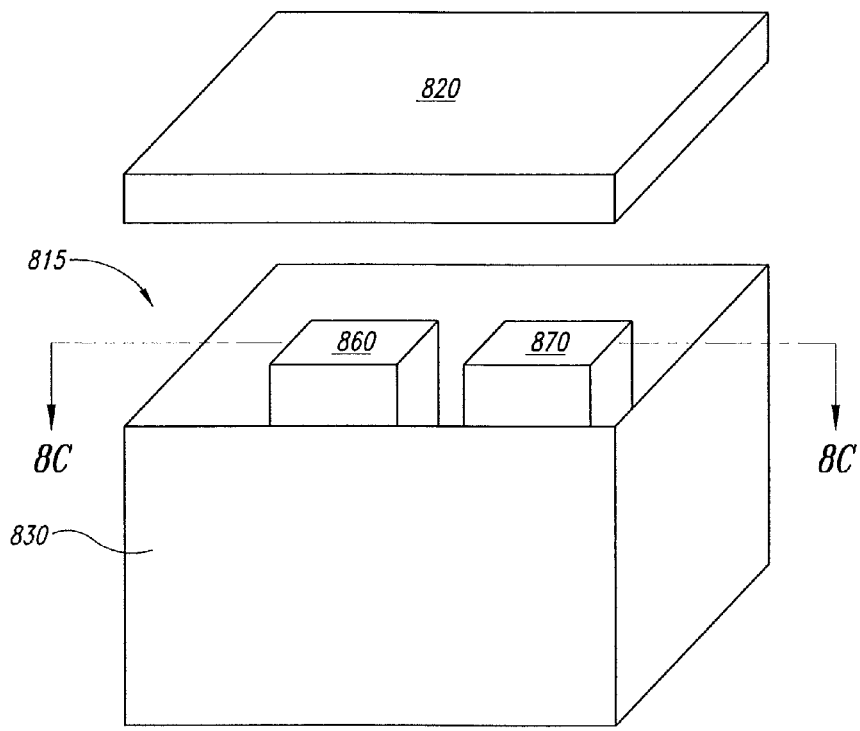
Figure 8C:
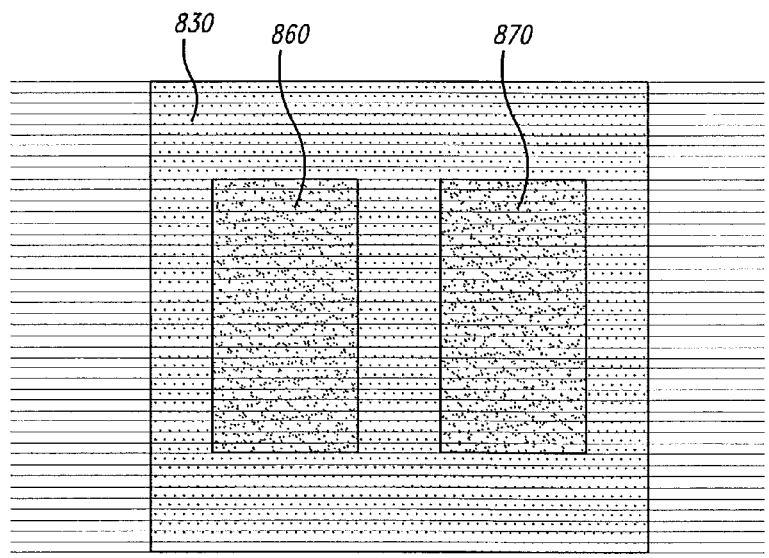

FIG. 8A illustrates a cubic or rectangular parallelepiped shaped oral dosage form with an exploded view of the top layer 820. The top layer 820 may contain several printed layers, or may be a single powder layer of thickness. The walls 830 of the ODS are also produced by layers of powder and binder liquid and can therefore be of any predetermined thickness and even of varying thickness. Internal geometry includes nested regions 840 and 850. These regions may be of any predetermined shape, may contain API or not, may contain different API from the closest nested component, or some variation thereof.

Another possible multi-region geometry comprises multiple compartments, in this case two compartments, which are not nested within each other. Each of them may contain different composition or amount of API. FIG. 8B shows such a multi-compartment dosage form 815 with two non-nested compartments 860 and 870, which may be of a rectangular parallelepiped shape. These are shown as further being surrounded by a surrounding region 836. Other geometric designs are also possible, such as including both nested and non-nested arrangements of regions in a dosage form. FIG. 8C illustrates a cross-sectional view along lines 8C-8C of FIG. 8B. The adjacent regions of varying composition 860, 870 are shown as well as the encapsulating region 830. In all cases, after manufacture of an article such as a 3DP printed article, the article can be compressed such as by uniaxial compression while maintaining the complex internal geometry.

Example 5

3DP Oral Dosage Forms with Internal Gradients of Composition

Examples so far have described the interior of the printed article or dosage form as comprising discrete regions within each of which the composition was essentially homogeneous. Other possible compositional variations that could be manufactured by 3DP include gradients of one or more substances in any direction.

The terms uniform composition and nonuniform composition and gradient, when used with a powder-assembly manufacturing process such as 3DP, have meaning on a size scale greater than the size of individual powder particles. In describing an article as being of uniform composition when it is manufactured by three-dimensional printing (3DP) starting from powder particles, it is meant that the article has uniform composition when composition is averaged over a size scale which is somewhat greater than the size of individual powder particles from which the article was made. This understanding is necessary because in 3DP individual powder particles may retain their identity, while binder substance deposited between individual powder particles such as by evaporation of a volatile liquid substance also may retain its own identity.

Thus, on a size scale comparable to the particle size, a 3DP printed article may exhibit nonuniformity as one moves from a powder particle to binder substance and then to another powder particle, but at a somewhat larger size scale the article may be said to be of uniform composition if manufactured similarly throughout. It is also possible to have different distinct regions so that the dosage form has a composition that is non-uniform on a size scale larger than a powder particle. The nonuniformity is determined by the concentration or composition of the deposited substances, on a size scale larger than the particle size, as a function of position within the dosage form. This may be achieved by appropriate programming of the deposition of binder liquid in the three-dimensional printing process described later, and can be produced repeatably each time the dosage form of the present invention is manufactured according to a particular set of instructions.

In terms of designing a dosage form having a gradient of composition of one or more substances, the gradient may exist in terms of how the local composition or concentration of the binder substance of API or in general the deposited solid substance varies as a function of position, with the local composition being understood to be averaged over a size scale which is somewhat greater than the size of individual powder particles.

Any dosage form would have a geometric center, and concentration of one or more components could be a function of distance from the geometric center of the dosage form, either by use of a dosage form having spherical symmetry or by use of a dosage form which lacks spherical symmetry but has a reasonably simple shape such as a circular cylinder or rectangular parallelepiped of not too extreme aspect ratio. Concentration is affected by which of several possible binder liquids is dispensed at a given location, how much of a given binder liquid is dispensed at a given location, etc. The dimension of space over which a dissimilarity of composition could be created would be related to the dimensions of the volume occupied by one dispensed drop or similar unit of dispensed binder liquid.

Achieving a gradient of composition could be achieved by appropriate programming of the instructions for building the 3DP printed article. This could include dispensing of specified fluids from specified dispensers. It could include the use of variable drop volume dispensing of fluids, if the dispenser or printhead is capable of that. For example, some piezoelectric drop-on-demand dispensers are capable of variable dispensed volume depending on the electrical waveform supplied to drive the dispenser.

An article such as a 3DP printed article containing gradients of API could then be uniaxially compressed using the techniques of the present invention and would retain its spatial distribution of composition subject to the already-experienced shrinkage along the axis of compression and possibly subject to the already-experienced minor rearrangement of material in directions perpendicular to the axis of compression.

If it is not desired to experience the minor rearrangement of material in directions perpendicular to the axis of compression, it would be possible to match void fractions of the various regions or match void fractions on a fairly continuous basis throughout the article similar to what was done in Example 3. This would be done by programming 3DP instructions such that wherever the deposited concentration of API was relatively large, the concentration of other deposited solids would be relatively small, and as the concentration of deposited API became smaller in certain places, the concentration of other deposited solids would be set to be relatively larger in those same places, so that everywhere the total concentration of deposited solids would be approximately constant. Attaining a situation where the concentration of total deposited solids was approximately constant everywhere throughout the article such as a 3DP printed article or in significant regions of the article such as a 3DP printed article means that during compression the article would essentially shrink only along the axis of compression and localized rearrangement of material in directions perpendicular to the axis of compression should be nearly zero.

Example 6

Increasing the API Concentration from Uniaxial Compression of 3DP Oral Dosage Form Example 6 focuses on the quantity of an Active Pharmaceutical Ingredient that can be packaged into a dosage form. This content may be expressed in a normalized sense, as mg of API per cc of API-containing region of the dosage form (mg/cc). Example 6 was performed using an API that was highly soluble in the binder liquid. The API was diclofenac sodium (Sigma Chemical Co.), which is highly soluble in methanol that was used as the solvent part of the binder liquid. In the experiments of this example, the entire article such as a 3DP printed article contained API, as opposed to the more complicated two-region construction of Example 2. The dosage form was also of a simpler shape than in the earlier Examples, namely circular cylinders with flat ends.

The powder bed consisted of 70-wt % Lactose and 30-wt % hydroxypropylmethylcellulose (HPMC) (Methocel K4M, Dow Chemical Co.) with a packing fraction of 0.412. The API solution printed into these tablets was 18 wt % diclofenac dissolved in methanol, along with 1 wt % polyvinyl pyrrolidone (PVP) which served as a binder substance. This API-containing binder liquid was printed everywhere in these printed articles. The articles were printed in a flat-ended cylinder shape of diameter 10.42 mm using 16 layers to give an overall height of 4.8 mm.

The printing parameters for printing the diclofenac sodium solution were a line spacing of 120 microns, a layer height of 300 microns, a flow rate of 0.97 g/min, a nozzle orifice diameter of 50.4 microns, a raster speed of 150 cm/sec and a modulation frequency of 42.0 kHz for the piezoelectric element which stimulates droplet breakoff in the Continuous Jet with Deflection printhead. The saturation parameter refers to a unit volume defined by one drop-to-drop spacing in the fast axis direction, by one line-to-line spacing in the slow axis direction, and by one layer thickness in the vertical direction. The saturation parameter describes how much of the void space in this unit volume is occupied by dispensed liquid. The above printing parameters combined to achieve a saturation parameter of 0.57. Each printing pass took approximately 2 minutes.

Four sets of articles or dosage forms containing the API substance diclofenac sodium were fabricated:

set 1: One printing pass was used. The dosage printed into each tablet was calculated, based on printing parameters, to be 22.08 mg of diclofenac.

set 2: Some of the first set of tablets were then pressed under uniaxial compression of 15,000 lbf/inch{circumflex over ( )}2 (psi) in a cylindrical tablet die 11 mm in inside diameter with flat end dies. The resulting pressed tablets were 11.17 mm in diameter and 1.78 mm in height.

set 3: The same printing conditions were then used to fabricate a third set of tablets by printing API solution four times into each layer instead of once as in the first set. After each printing pass, the bed was allowed to dry for approximately 3 minutes between print passes. Each layer took approximately 15 minutes to build. A parameter called apparent saturation is defined as the number of printing passes per layer times the saturation printed during each individual printing pass. Here it had the value of 4×0.566 or 2.26. The dosage printed into each tablet was calculated, based on printing parameters, to be 88.16 mg of diclofenac.

set 4: Some of the third set of tablets were pressed under uniaxial compression of 15,000 psi as just described. The resulting tablets were 11.17 mm in diameter and 2.33 mm in height.

In order to measure API content, each tablet was allowed to completely dissolve in 900 mL of phosphate buffer solution, having a pH of 7.4, at 37° C. Absorbance was measured using a spectrophotometer (Beckman DU 640) using the peak absorbance wavelength for diclofenac sodium, which was 275 nm. An absorbance/concentration calibration experiment conducted for absorbance of diclofenac sodium in phosphate buffer solution showed a linear dependence of absorbance on API concentration for a wide range of concentrations including the range of current interest.

By this method, the first and second sets of diclofenac tablets, printed with a saturation of 0.57, were measured to contain 21.98 mg+/−0.22 mg of API in each tablet. Combining this measured API quantity with measured external dimensions of compressed or non-compressed tablets gives an API concentration or density "delta" of API in either the noncompressed article such as a 3DP printed article or the compressed dosage form. The non-compressed single-pass tablets contained an API concentration $\delta$=53.74 mg/cc, and the compressed single-pass tablets contained an API concentration $\delta$=115.08 mg/cc.

The API concentration was more than doubled by compression, because before compression the void fraction was slightly less than half. The third and fourth sets of diclofenac tablets, printed with an apparent saturation of 2.26 as a result of four-pass printing, were similarly determined to contain 87.98 mg+/−0.28 mg in each tablet. As would be expected, since these tablets were printed with four passes rather than one, this magnitude of the API content was almost exactly four times that of the single-pass-printed tablets. As far as API concentration, the non-compressed tablets contained a API concentration of 215.11 mg/cc and the compressed tablets contained a API concentration of 350.52 mg/cc.

In this experiment the improvement in API concentration as a result of compression was not a quite a doubling, probably because in this case the void spaces were already somewhat filled by the multi-pass printing and so the actual void fraction prior to compression was less than half. Comparing the compressed four-pass-printed dosage forms to the compressed single-pass-printed dosage forms, the API concentration for the four-pass-printed dosage forms was approximately triple that for the compressed single-pass-printed dosage forms. Thus, there is advantage in multi-pass solution printing, as it allows filling more of the initial void volume with API before that volume is removed by compression, or in other words, more API is deposited relative to a given amount of excipient powder.

Table 3 summarizes the results from the fabrication of dosage forms using the diclofenac solution.

TABLE 3

δ VALUES (MG/CC) FOR 3DP PRINTED ARTICLES OR DOSAGE FORMS WITH SINGLE-PASS AND FOUR-PASS PRINTING, BEFORE AND AFTER COMPRESSION

| | Solution (18 wt % diclofenac) | |
|---|---|---|
| | 1 Print Pass $S = 0.566$ | 4 Print Passes $S_{app} = 2.26$ |
| Un-Pressed | 53.74 | 215.11 |
| Pressed | 115.08 | 350.52 |

Figure 3:
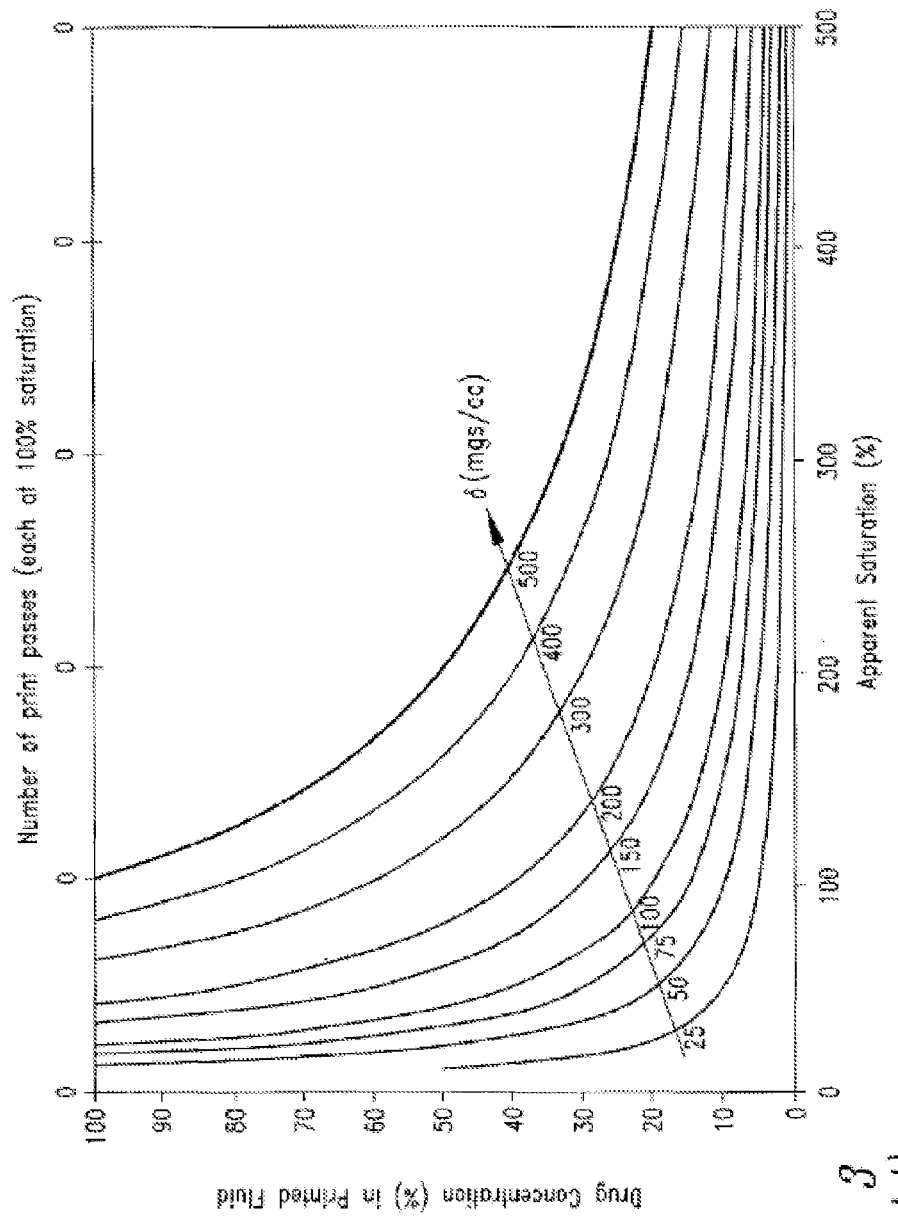
FIG. 3 is a graph illustrating the same API loading data as in FIG. 3, but in a form normalized by API-containing volume in accordance with the prior art.
Figure 9:
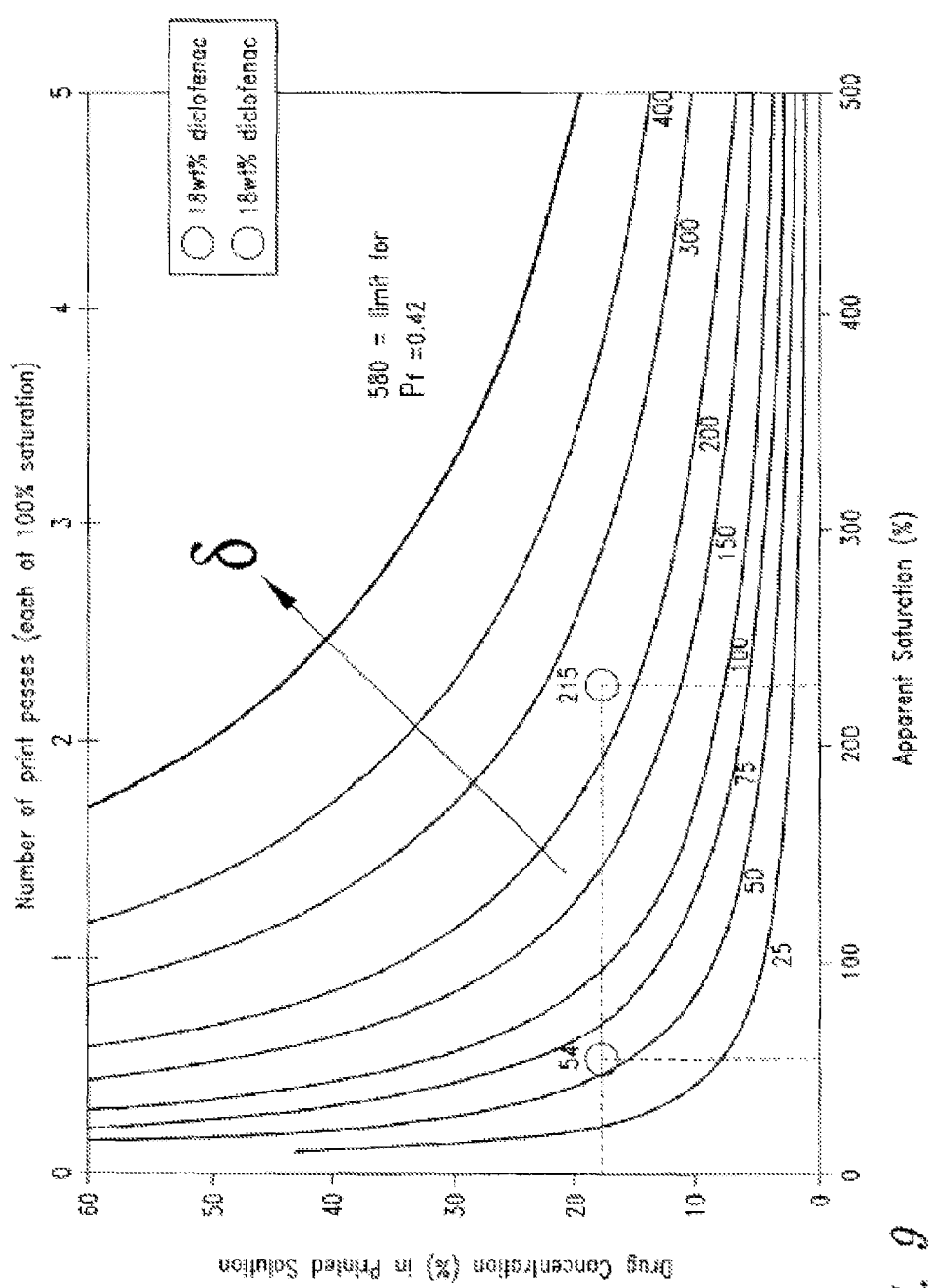
FIG. 9 is a graph illustrating concentrations of API loading, prior to the uniaxial compression operation, for two specific experiments, plotted on the same axes as FIG. 4 in accordance with principles of the present invention.

FIG. 9 shows the results for experimentally measured dosage per unit volume, $\delta$, for the non-compressed tablets in the experiments in this Example, added onto the same form of plot with calculated $\delta$ contours as was displayed in FIG. 3. FIG. 9 shows the $\delta$ values achieved both before and after compression for the experiments described in this Example. Pressing enhances the API concentration by decreasing the volume for the same dosage. The arrows in FIG. 10 indicate how the value of $\delta$ changes in each experiment when the tablets are pressed.

It can be seen that uniaxial pressing of articles originally made by 3DP has greatly increased the values of API concentration (delta) by decreasing the tablet volume for a fixed dosage. The highest value of "delta" obtained for solution-printed dosage form was 351 mg/cc for dosage forms that were both 4x-printed and uniaxially compressed. The theoretical limit for attainable API concentration, for the conditions used in this experiment, such as the initial void fraction of the powder and the physical properties of the API substance, was 580 mg/cc. This theoretical limit represents what would occur if all of the void space between the powder particles as originally spread was filled with API, which would then make compression unnecessary because there would be no void space to remove. In the compressed dosage form there was also essentially no void, but there is a smaller percentage of deposited API because of incomplete filling and hence there was a larger percentage of powder and than in the theoretical limiting case. Thus, this case of the highest achieved "delta" represents attaining an API concentration that is approximately 60% of the theoretical limit.

Example 7

Improving the Consistency of the Release Profile of the ODF

Figure 10:
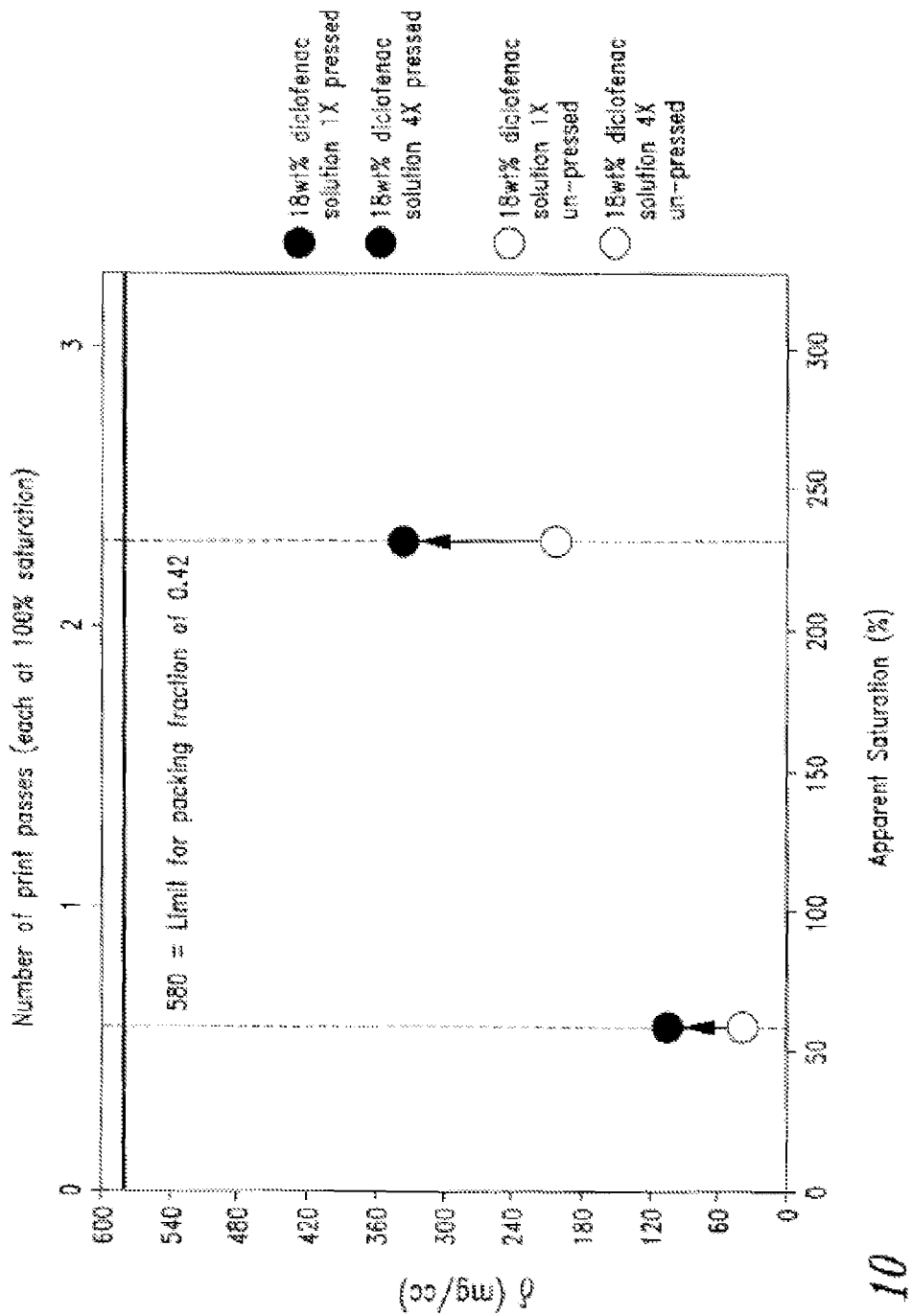
FIG. 10 is a graph illustrating concentrations of API loading for the two specific experiments both before and after uniaxial compression in accordance with principles of the present invention.

A dosage form of the present invention, which may be of interest, may comprise an interior region, containing API, which is surrounded by a shell as illustrated in FIG. 5 and FIG. 10. The shell may influence the release profile of API contained in the interior region. Given the limitations on overall dimensions of a dosage that can be comfortably swallowed by a patient, the shell may have a limitation on its thickness such as approximately 1 mm or perhaps 2 mm maximum thickness.

In an uncompressed 3DP ODF, the number of drops or voxels which correspond to this shell thickness may be somewhere in the range of 2 to 10 drops or voxels. In an uncompressed 3DP ODF, especially if the number of drops or voxels is at the lower end of this range, there are possibilities for pinhole leaks through the shell either at the time of manufacture or after a certain amount of residence time in the gastrointestinal tract. Pinhole leaks are essentially connected void spaces that form a pathway across the thickness of the shell from one side of the shell to the other. Even one or a small number of pinhole leaks anywhere in the shell could cause the release profile of the API from that particular dosage form to be different from what was intended. It is likely that compression of an article such as a 3DP printed article using a high pressure, such as a pressure sufficient to compact the article to a final void fraction of less than 5%, would compact the shell region sufficiently to compact and eliminate essentially all pinhole leaks or potential pinhole leaks that may be present.

Thus, it is believed that compression such as uniaxial compression after a detailed manufacturing process such as 3DP, can improve the consistency of the drug release profile of a dosage form. Compression may also result in a slower overall release rate than the corresponding non-compressed situation, due to the reduced access of bodily fluids to the API. The shell may comprise a substance that dissolves or degrades in digestive fluids at a desired rate, or a substance that dissolves or degrades only in fluids of a certain pH.

Example 8

Effect of Partial Compression of a 3DP Oral Dosage Form

Examples so far have described that after production of an article, such as a 3DP printed article, the article may be compressed using a compressive force sufficiently large as to eliminate essentially all of the void space and result in a dosage form that is essentially fully dense, as has already been described. However, this is not the only possible way of using compression after a fabrication process such as 3DP. In general, the release rate of any API from any type of dosage form is significantly influenced by the porosity of the dosage form or in particular the porosity of the shell if the dosage form comprises a shell. Pores provide routes for bodily fluids to access and dissolve portions of the dosage form.

The uniaxial compression process provides an adjustable parameter by which the porosity of an article or dosage form can be adjusted so as to have any desired value within a wide range. The final porosity would have to have a porosity that is at most the porosity in the article such as a 3DP printed article. The smallest possible value of porosity after compression would be essentially zero porosity. It is possible that for certain purposes an intermediate value of porosity may be desirable, rather than full compaction. The intermediate value could be chosen so that some of the benefits of compression are obtained, and the resulting release profile of the dosage form is a desired release profile. The release profile of a partially-compacted dosage form can be expected to be faster than what occurs for full compaction. Even if compression is only performed to less than full density, there will probably still be significant improvement in surface finish.

Further Discussion

The dosage form manufactured by the present invention may be an oral dosage form. It could also in general be any type of dosage form including, but not limited to, an implantable device. Dosage forms made by the present invention could also be given post-processing steps such as coating, marking, being packaged in gelatinous capsules, etc., such as to provide a surface which becomes slippery when wet for ease of swallowing.

API that may be used in dosage forms of the present invention includes essentially any type of API suitable for administration by existing dosage forms. Specifically, API may include pain relieving API of various types, including pain relievers for cancer, pain relievers for arthritis and pain relievers for other diseases; hormones; API to combat hypertension, Parkinson's disease, Attention Deficit Disorder, asthma and other diseases, all of which may benefit from detailed control of release profiles of API. It is possible for more than one Active Pharmaceutical Ingredient to be incorporated into a single dosage form. It is possible for more than one API to be dissolved in a binder liquid.

Instead of dispensing the Active Pharmaceutical Ingredient with the dispensed binder liquid, it would be possible for the Active Pharmaceutical Ingredient to be mixed in with the powder that is spread, and then to be bound by the binder liquid. The uniaxial compression step would then follow. This would primarily be suitable for situations where there is no need for compositional variation within the interior of the dosage form and the pharmaceutical is not particularly expensive.

In any multi-pass printing, although it might be desirable to have complete drying of the dispensed liquid before the next dispensing of liquid onto the same layer, it would be more time-efficient to provide for nearly-complete drying rather than complete drying before spreading of the next layer, and in fact it might even be better by promoting better layer-to-layer adhesion. Appropriate choice of the saturation parameter for subsequent printings could be made, along with suitable timing.

In general, any type of printhead can be used in connection with the present invention. This includes microvalves, piezoelectric drop-on-demand, Continuous-Jet with Deflection, and also boiling (bubble-jet) printheads if the substances involved are not thermally damaged. While dispensing of binder liquid may frequently be thought of as occurring by dispensing of discrete drops, this is actually not necessary. Dispensing could be performed with fluid streams that are discrete drops, or connected drops, or continuous streams, or in general a fluid stream of any appearance.

This technique of uniaxial compression affords the possibility of achieving larger values of API concentration in 3D printed dosage forms than were previously possible, and hence makes 3DP more attractive for this purpose than it previously was. Limitations on API loading have long been viewed as a limitation on the use of 3DP for making oral dosage forms. API's vary widely in their potency or the amount of API which must be packaged into a dosage form, but for some API's the improvement in API loading or concentration achievable by this invention could make the difference between 3DP being practical or impractical for that API. Furthermore, the present invention can completely solve the problem of poor surface finish while retaining all the advantages of 3DP in terms of placement of compositional variations within a dosage form. The uniaxial compression process of the present invention is also fast and well suited to mass production.

All references cited herein are hereby incorporated by reference in their entirety.

From the foregoing it will be appreciated that, although specific embodiments of the invention have been described herein for purposes of illustration, various modifications and combinations thereof may be made without deviating from the spirit and scope of the invention. Accordingly, the invention is not limited except as by the appended claims.

What is claimed is:

1. A process for the manufacture of a uniaxially compressed pharmaceutical composition, the process comprising:

1) preparing a three-dimensionally printed pharmaceutical composition having a predetermined spatially nonuniform internal composition before uniaxial compression that is substantially the same as the spatially nonuniform internal composition after uniaxial compression comprising powder particles bound together by a binding substance; and 2) uniaxially compressing comprising a) placing the three-dimensionally printed pharmaceutical composition in a die assembly having confining surface which substantially surround the dosage form from all directions except for one direction and, in that direction, the die assembly having an opening which defines an axis of compression and b) moving a ram along the axis of compression into the opening, thereby uniaxially compressing the dosage form having a surface finish having a peak-to-valley dimension wherein the peak-to-valley dimension is less than or approximately equal to 3 microns to form the uniaxially compressed pharmaceutical composition having a void fraction of less than 5%.

2. The process of claim 1, wherein the pharmaceutical composition is uniaxially compressed by a die assembly comprising a lower die having a lower die outside geometry, and a sleeve having a sleeve inside geometry, and wherein a ram having a ram outside geometry, and wherein the lower die outside geometry and the ram outside geometry are both closely fitting with respect to the sleeve inside geometry.

3. The process of claim 2, wherein the ram outside geometry, the lower die outside geometry and the sleeve inside geometry are all cylindrical.

4. The process of claim 2, wherein the lower die has a lower die surface facing the the pharmaceutical composition and the ram has a ram surface facing the pharmaceutical composition, and the lower die surface or the ram surface or both are generally curved.

5. The process of claim 2, wherein the lower die has a lower die surface facing the pharmaceutical composition and the ram has a ram surface facing the pharmaceutical composition, and the lower die surface or the ram surface or both are generally flat.

6. The process of claim 2, wherein the lower die surface and the sleeve inner surface and the ram have surface finishes which are smoother than or approximately equal to 2 microns rms.

7. The process of claim 2 further comprising including depressed or raised markings on the lower die surface or ram surface or both.

8. The process of claim 2, wherein the uniaxially compressed dosage form has a shape selected from the group consisting of: cylindrical with flat ends, cylindrical with curved ends, rectangular prismatic with flat ends, rectangular prismatic with curved ends, elliptical prismatic with flat ends, elliptical prismatic with curved ends, ellipsoidal, spherical.

9. The process of claim 2, wherein the die and the ram and the sleeve all have respective hardnesses, and the pharmaceutical composition has a hardness, and the hardnesses of the die and the ram and the sleeve are all greater than the hardness of the pharmaceutical composition.

10. The process of claim 2, wherein the lower die has a lower die surface and the ram has a ram surface, and the pharmaceutical composition has a pharmaceutical composition top surface and an dosage form bottom surface, and the lower die surface approximately matches the dosage form bottom surface, and the ram surface approximately matches the pharmaceutical composition top surface.

11. The process of claim 2, wherein the lower die and the sleeve are integral components.

12. The process of claim 1, wherein the step of uniaxially compressing comprises providing a uniaxially compressed pharmaceutical composition with improved surface characteristics and increased Active Pharmaceutical Ingredient loading as compared to Active Pharmaceutical Ingredient loading of the dosage form before compression.

13. The process of claim 1, wherein the step of "uniaxially compressing" further comprises compressing the pharmaceutical composition uniaxially while in substantially all other directions the pharmaceutical composition is confined against rigid surfaces.

14. The process of claim 1, wherein the volume shrinkage and dimensional shrinkage which occurs during uniaxial compression are approximately 50%.

15. The process of claim 1, wherein rearrangement of material in the pharmaceutical composition in directions other than the axis of uniaxial compression is smaller than the dimensional changes of the pharmaceutical composition along the axis of compression.

16. The process of claim 1, wherein before uniaxial compression the void fraction in the various regions of the pharmaceutical composition are equal to each other.

* * * * *